(12) United States Patent
Kawasugi

(10) Patent No.: US 7,625,916 B2
(45) Date of Patent: Dec. 1, 2009

(54) MEDICINAL COMPOSITION

(76) Inventor: Kaname Kawasugi, 26-10-405, Higashi-oi 5-chome, Shinagawa-ku Tokyo (JP) 140-0011

( * ) Notice: Subject to any disclaimer, the term of this patent is extended or adjusted under 35 U.S.C. 154(b) by 122 days.

(21) Appl. No.: 10/572,557

(22) PCT Filed: Sep. 17, 2003

(86) PCT No.: PCT/JP03/11847

§ 371 (c)(1), (2), (4) Date: Mar. 17, 2006

(87) PCT Pub. No.: WO2005/027967

PCT Pub. Date: Mar. 31, 2005

(65) Prior Publication Data

US 2007/0105910 A1    May 10, 2007

(51) Int. Cl.
*A61K 31/51* (2006.01)
*A61K 31/44* (2006.01)
*A61K 31/425* (2006.01)

(52) U.S. Cl. .................. 514/276; 514/342; 514/350; 514/369; 514/866

(58) Field of Classification Search ............... 514/276, 514/342, 369, 350, 866
See application file for complete search history.

(56) References Cited

U.S. PATENT DOCUMENTS

| 3,502,674 | A | | 3/1970 | Takamizawa et al. | |
| 4,687,777 | A | * | 8/1987 | Meguro et al. | 514/342 |
| 5,002,953 | A | * | 3/1991 | Hindley | 514/275 |
| 5,977,073 | A | * | 11/1999 | Khaled | 514/19 |
| 6,166,219 | A | * | 12/2000 | Yamasaki et al. | 548/309.4 |
| 6,251,926 | B1 | * | 6/2001 | Momose et al. | 514/364 |
| 6,660,293 | B2 | * | 12/2003 | Giordano et al. | 424/439 |

FOREIGN PATENT DOCUMENTS

| FR | 2832064 A1 * | 5/2003 |
| WO | 02/051441 | 7/2002 |

OTHER PUBLICATIONS

Tamai, Hiroshi, "Diabetes and Vitamin Levels", Japanese Journal of Clinical Medicine, vol. 57, No. 10, pp. 200-203, 1999.
Hashizume, Naotaka, "Vitamin B1 Deficiency", Igaku no Ayumi, vol. 198, No. 13, pp. 949-952, 2001.

* cited by examiner

*Primary Examiner*—Kevin Weddington
(74) *Attorney, Agent, or Firm*—Oblon, Spivak, McClelland, Maier & Neustadt, L.L.P.

(57) ABSTRACT

A medicinal composition which comprises an insulin resistance-improving drug and vitamin $B_1$ or derivative thereof. In this medicinal composition, the side effects of the insulin resistance-improving drug such as edema, heart enlargement, anemia, etc. are prevented by using vitamin $B_1$ or its derivative together. It is usable as a remedy for diabetes, a remedy for lifestyle related diseases, an anti-tumor agent, an anti-rheumatoid drug and so on.

6 Claims, No Drawings

MEDICINAL COMPOSITION

TECHNICAL FIELD

The present invention relates to a medicinal composition, and more particularly it relates to a medicinal composition which comprises an insulin resistance-improving drug as a major ingredient and in which the side-effects including edema, heart enlargement and anemia caused thereby are reduced.

BACKGROUND ART

Insulin resistance is a pathologic condition which requires an excess amount of insulin over the normal amount for gaining a variety of actions of insulin at the level of cells, organs and individuals. This pathologic condition is a state meaning decrease of the insulin sensitivity in liver, skeletal muscle and fat tissue and characteristic in type II diabetes mellitus with failure of insulin secretion. Insulin resistance is much involved in formation of a pathologic condition of lifestyle-related diseases such as hypertension or hyperlipemia in addition to diabetes mellitus and impaired glucose tolerance, and its improvement is becoming clinically more important.

As drugs which can possibly be used as insulin resistance-improving drugs inhibiting insulin resistance, compounds which have a γ-agonist activity of peroxisome proliferator-activated receptor (PPAR)(hereinafter referred to as "PPAR-γ activation promoting compound"), which is a nuclear receptor, have been known and some of them have been employed for type II diabetes mellitus. These compounds have a blood sugar-lowering effect in addition to lipid metabolism-improving effect.

As for PPAR-γ activation promoting compounds, thiazolidine-type compounds and non-thiazolidine-type compounds are known. The thiazolidine-type compound includes troglitazone, pioglitazone, rosiglitazone, CS-011, and the like; and the non-thiazolidine-type compound includes TAK-559; FK-614, and the like.

It has been considered that these insulin resistance-improving drugs primarily act on adipocytes through PPARγ to accelerate differentiation of the adipocytes and inhibit an insulin resistance causative factor such as TNF-α to improve the insulin resistance. Details are not clear.

In this connection, the first launched insulin resistance improving drug in the world was a thiazolidine-type compound troglitazone, but this was withdrawn because of occurrence of serious hepatic disturbance. Subsequently, the same thiazolidine compounds, pioglitazone and rosiglitazone, were developed and at present these two drugs have been used oversea as insulin resistance improving drugs; in Japan, pioglitazone alone has been used.

However, there was a problem in the insulin resistance improving drugs since they have other side-effects, i.e., edema, heart enlargement, anemia, and soon, particularly edema. That is, in pioglitazone, rosiglitazone and troglitazone, the side-effects such as edema and anemia have been observed in several percentage, and in pioglitazone congestive heart failure has been recognized. This is one of the reasons why they are not so used domestically in Japan though they have a high usefulness as insulin resistance-improving drugs.

Such edema as a side-effect has been observed in all of the so far known thiazolidine-type compounds under development; when the edema occurs as side effect, the administration has to be stopped in some cases, and in another case a diuretic is required; thus, these have big problems in using as drugs.

As mentioned above, the insulin resistance-improving drugs have problems of the side effects such as edema, heart enlargement and anemia. Thus, the purpose of the invention is to provide a technique for reducing such side effects.

DISCLOSURE OF INVENTION

In order to solve the above problems, the present inventor worked assiduously to investigate the cause of the above-mentioned side effect in the insulin resistance-improving drugs and found that in vivo vitamin $B_1$ was relatively deficient due to administration of an insulin resistance-improving drug. It was also found that the simultaneous administration of the insulin resistance-improving drug with vitamin $B_1$ was effective in prevention of the above side effect. Thus, the invention was completed.

That is, the invention provides a medicinal composition which comprises an insulin resistance-improving drug and vitamin $B_1$ or its derivative.

BEST MODE FOR CARRYING OUT THE INVENTION

As the insulin resistance-improving drug used in the medicinal composition of the invention, compounds having a PPARγ agonist activity are exemplified. More specifically, PPAR-γ activation-promoting compounds of thiazolidine type such as pioglitazone, rosiglitazone, CS-011, and the like, and PPAR-γ activation-promoting compounds of non-thiazolidine type such as TAK-559, FK-614, and the like are included. These compounds, if required, may be converted into such derivatives as pharmaceutically acceptable salts of them.

Particularly preferred insulin resistance-improving drugs are PPAR-γ activation-promoting compounds of thiazolidine type, pioglitazone and rosiglitazone as well as their derivatives such as addition salts.

On the other hand, vitamin $B_1$ (thiamine) used in the medicinal composition of the invention is a well-known water-soluble vitamin, which has almost no side effect even in overdose and of which the cost is low. The vitamin $B_1$ derivatives are also known, including, for example, fursultiamine, benfotiamine, octotiamine, prosultiamine, bisbentiamine, dicetiamine hydrochloride, thiamine hydrochloride, thiaminedisulfide, co-carboxylase, and the like.

In producing the medicinal composition of the invention, the above-mentioned insulin resistance-improving drug and vitamin $B_1$ or its derivative (hereinafter, referred to as "Vitamins $B_1$") are combined with a suitable pharmaceutically acceptable carrier, then mixed, and formulated into a desired pharmaceutical preparation.

The amount of the insulin resistance-improving drug to be combined for a dose unit of medicinal composition of the invention is preferably from 5 to 300 mg, and the amount of Vitamins $B_1$ to be combined is preferably from 1 to 500 mg.

There is no particular limitation in the combination ratio between the insulin resistance-improving drug and Vitamins $B_1$, and Vitamins $B_1$ may be used in an amount of about 0.01 to 200 parts by weight, preferably about 0.05 to 40 parts by weight, for one part by weight of the insulin resistance-improving drug.

More specifically, when pioglitazone hydrochloride which is only one insulin resistance-improving drug available in Japan is used in the medicinal composition of the invention, a preferred combination is illustrated as follows. That is, pioglitazone hydrochloride is incorporated in one unit dose of the pharmaceutical preparation in the amount of 15-45 mg, which amount is a dose (oral administration) of pioglitazone hydrochloride for once a day. On the other hand, when fursultiamine is used as Vitamins $B_1$ in combination, it may be incorporated in the amount of 5-100 mg for one unit dose. This amount may also be adapted in a case in which fursultiamine is replaced by benfotiamine as another Vitamins $B_1$.

The medicinal composition of the invention may be formulated into solid preparations such as powders, pellets, granules, tablets, capsules, and so on, or liquid preparations such as liquids and solutions.

There is no particular limitation in carriers used in producing the medicinal composition of the invention, and a powder or liquid carrier may be employed according to the objective formulation. In addition, if necessary, a suitable additive used in the pharmaceutical field may be added.

Though mixture preparations were used as examples in the above description, needless to say, the insulin resistance-improving drug and the Vitamins $B_1$ may respectively be formulated independently, and they may be used in a combined preparation.

[Effect]

Regarding the mechanism of edema formation as a side effect in the insulin resistance-improving drug, it has been reported that there are possibilities such as increase of Na reabsorption-accelerating action of insulin in renal, direct accelerating action to a $NaHCO_3$-co-transporter in renal, sthenic effect in vascular permeability by increase of the blood VEGF level, and so on. The heart enlargement and anemia are considered due to increase of the amount of circulating plasma caused by them.

It has been found by the present inventor that one of causes of the above side effects exists in increase of vitamin $B_1$ demand in the living body induced by the insulin resistance-improving drug.

Thus, the effect of the invention is to prevent and improve the relative deficiency of vitamin $B_1$ in the living body by administering vitamin $B_1$ along with an insulin resistance-improving drug and reduce the side effects such as edema, heart enlargement, anemia, etc.

EXAMPLES

The invention will be explained in more detail by the following examples which are not intended as a limitation thereof.

Example 1

Repeated oral administration test for 10 days using rats:

SD-Family rats (Crj:CD:IGS) of 8 weeks of age were divided into two groups; in one group, pioglitazone hydrochloride is orally administered at a dose of 240 mg/kg/day for 10 days forcibly through a gastric probe, and the in the other group, 240 mg/kg/day of pioglitazone hydrochloride and 100 mg/kg/day of benfotiamine were administered in the same manner. After termination of the administration, the blood was collected from the rats and the hemoglobin (Hb) value was determined. Then, the rats were killed, and their hearts were weighed (relative weight). Table 1 shows the result regarding the blood Hb, and Table 2 shows the weight ratio of the heart to the body weight.

TABLE 1

| Administration | Blood Hb conc. before administration (g/dl) | Blood Hb conc. after administration (g/dl) |
|---|---|---|
| Pioglitazone HCl alone | 12.9 | 13.6 |
| Pioglitazone HCl + Benfotiamine | 12.9 | 14.1 |

TABLE 2

| Administration | Weight ratio of the heart to the body weight (%) |
|---|---|
| Pioglitazone HCl alone | 0.35 |
| Pioglitazone HCl + Benfotiamine | 0.31 |

As clearly seen from Table 1, a tendency of improvement of hemoglobin decrease (anemia) was recognized in the benfotiamine-combined group in comparison with the group to which pioglitazone hydrochloride alone was administered.

As shown in Table 2, a tendency of improvement in the heart weight gain (heart enlargement) was recognized in the benfotiamine-combined group, in which the relative heart weight ratio after administration is lower than that in the group to which pioglitazone hydrochloride alone was administered.

From these results, it was shown that the combined use of benfotiamine can inhibit the side effect caused by sole administration of pioglitazone hydrochloride.

INDUSTRIAL APPLICABILITY

The medicinal composition of the invention, in which an insulin resistance-improving drug is used in combination with Vitamins $B_1$, is not accompanied by the side effect such as edema, heart enlargement and anemia, though the insulin resistance-improving drug is contained as a major drug; in addition, no decrease of the drug effect is recognized.

Vitamins $B_1$ used together shows almost no side effect even in overdose and is available in relatively low cost. Thus, the medicinal composition of the invention is superior in safety and economical point of view as medicine.

Therefore, the medicinal composition of the invention can be used to decrease the blood sugar level for type II diabetes mellitus.

The insulin resistance-improving drug contained in the medicinal composition of the invention has a lipid metabolism improving effect, anti-tumor effect and anti-rheumatoid effect, and can be used as a remedy for diabetes mellitus, remedy for lifestyle related diseases, anti-tumor agent, anti-rheumatoid drug, and so on.

The invention claimed is:

1. A medicinal composition comprising an insulin resistance-improving drug and vitamin $B_1$ or derivative thereof in an amount effective for inhibiting at least one side effect of said insulin resistance-improving drug, which side effect is selected from the group consisting of edema, heart enlargement and anemia, and wherein the insulin resistance-improving drug is selected from the group consisting of pioglitazone, rosiglitazone and CS-011, and salts thereof.

2. The medicinal composition claimed in claim 1, wherein the insulin resistance-improving drug is pioglitazone.

3. The medicinal composition claimed in claim 1, wherein the insulin resistance-improving drug is rosiglitazone.

4. The medicinal composition claimed in claim 1, wherein the insulin resistance-improving drug is CS-011.

5. The medicinal composition claimed in claim 1, comprising 5 to 300 mg of insulin resistance-improving drug, and 1 to 500 mg of vitamin $B_1$ or derivative thereof for one unit dose.

6. A method comprising administering the medicinal composition as claimed in claim 1 in an effective amount to a subject in need thereof.

* * * * *